United States Patent
Jäger et al.

(10) Patent No.: US 11,155,844 B2
(45) Date of Patent: *Oct. 26, 2021

(54) PROCESS FOR THE PRODUCTION OF ORTHO-AMINOBENZOIC ACID AND/OR ANILINE FROM FERMENTABLE SUBSTRATE USING RECOMBINANT YEAST

(71) Applicant: Covestro Deutschland AG, Leverkusen (DE)

(72) Inventors: Gernot Jäger, Cologne (DE); Amgad Salah Moussa, Bad Säckingen (DE); Simon Klaffl, Düsseldorf (DE); Thomas Hamedinger, Leverkusen (DE); Wolf Kloeckner, Cologne (DE); Swantje Behnken, Sacramento, CA (US)

(73) Assignee: Covestro Deutschland AG, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/062,706

(22) PCT Filed: Dec. 14, 2016

(86) PCT No.: PCT/EP2016/081021
§ 371 (c)(1),
(2) Date: Jun. 15, 2018

(87) PCT Pub. No.: WO2017/102853
PCT Pub. Date: Jun. 22, 2017

(65) Prior Publication Data
US 2018/0371512 A1    Dec. 27, 2018

(30) Foreign Application Priority Data
Dec. 18, 2015  (EP) ..................................... 15201326
Feb. 29, 2016  (EP) ..................................... 16157777

(51) Int. Cl.
*C12P 13/04*    (2006.01)
*C12P 13/00*    (2006.01)
*C12N 9/10*     (2006.01)

(52) U.S. Cl.
CPC ............ *C12P 13/04* (2013.01); *C12N 9/1077* (2013.01); *C12P 13/001* (2013.01); *C12Y 204/02018* (2013.01)

(58) Field of Classification Search
None
See application file for complete search history.

(56) References Cited

FOREIGN PATENT DOCUMENTS

| EP | 0549421 A1 | 6/1993 |
|---|---|---|
| WO | WO-2011050326 A1 | 4/2011 |
| WO | WO-2013103894 A1 | 7/2013 |
| WO | WO-2015124686 A1 | 8/2015 |
| WO | WO-2015124687 A1 | 8/2015 |
| WO | WO2015160257 | * 10/2015 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Wang et al. Chapter 6. Bioreactor Engineering. Bioprocessing for Value-Added Products from Renewable Resources. Shang-Tian Yang (Editor), Elsevier. 2007 (Year: 2007).*
Fujita et al. FEMS Yeast Research, vol. 6, Issue 5, Aug. 2006, pp. 744-750 (Year: 2006).*
Furter et al. Nucleic Acids Res. Aug. 26, 1986;14(16):6357-73 (Year: 1986).*
International Search Report for PCT/EP2016/081021 dated Apr. 12, 2017.
Written Opinion of the International Searching Authority for PCT/EP2016/081021 dated Apr. 12, 2017.
Düvel et al., "A single point mutation in the yeast TRP4 gene affects efficiency of mRNA 34 end processing and alters selection of the poly(A) site", Nucleic Acids Research, vol. 27, No. 5, 1999, pp. 1289-1295.
International Preliminary Report on Patentability received for PCT Patent Application No. PCT/EP2016/081021, dated Jun. 28, 2018, 14 pages.
Kuepper, J. et al., "Metabolic Engineering of Pseudomonas putida KT2440 to Produce Anthranilate from Glucose", Frontiers in Microbiology, vol. 6. Article No. 1310, 2015, pp. 1-9.

* cited by examiner

*Primary Examiner* — Christian L Fronda
(74) *Attorney, Agent, or Firm* — Faegre Drinker Biddle & Reath LLP (57) ABSTRACT

The present invention relates to the production of o-aminobenzoic acid from fermentable substrates using yeast cells.

10 Claims, 7 Drawing Sheets

PROCESS FOR THE PRODUCTION OF ORTHO-AMINOBENZOIC ACID AND/OR ANILINE FROM FERMENTABLE SUBSTRATE USING RECOMBINANT YEAST

CROSS-REFERENCE TO RELATED APPLICATIONS

This application is a national stage application (under 35 U.S.C. § 371) of PCT/EP2016/081021, filed Dec. 14, 2016, which claims benefit of European Application Nos. 15201326.4, filed Dec. 18, 2015, and 16157777.0, filed Feb. 29, 2016, all of which are incorporated herein by reference in their entirety.

The present invention relates to the production of o-aminobenzoic acid from fermentable substrates using yeast cells.

Currently, there is no renewable or biologically derived source of o-aminobenzoate or the corresponding acid commercially available. O-aminobenzoate is a natural intermediate of the shikimate acid pathway and a precursor for the biosynthesis of the aromatic amino acid L-tryptophane. A chemical conversion of o-aminobenzoate to aniline has been described in WO 2015/124687.

Current production methods of aniline rely on chemical synthesis from petroleum-derived raw-materials. Such petroleum-derived raw materials are not renewable as opposed to raw materials which are renewable, such as the renewable resource "biomass". The chemical synthesis of aniline is a multi-step process. The several reaction steps involved in the production of aniline result in high production costs. Moreover, the conventional, i.e. chemical, synthesis of aniline is associated with hazardous intermediates, solvents, and waste products which can have substantial impacts on the environment. Non-specific side-reactions on the aromatic-ring result in the reduction of the product yield, thus further increasing the production costs. Petroleum-derived raw materials are influenced by cost fluctuations resulting from the global petroleum price.

WO 2015/124687 discloses a concept of producing biologically-derived o-aminobenzoate and aniline. Two conversion steps are applied: (1) the fermentative production of o-aminobenzoate and (2) the subsequent catalytic conversion of o-aminobenzoic acid into aniline. The overall process concept comprises the following processing steps:
a) producing o-aminobenzoate by fermentation of a raw material comprising at least one fermentable carbon substrate using a recombinant bacterial host cell that is capable of converting said raw material comprising at least one fermentable carbon substrate to o-aminobenzoate biologically, wherein said o-aminobenzoate comprises anthranilate anion, (followed by cell removal),
b) converting said o-aminobenzoate from said anthranilate anion in the cell free aqueous fermentation broth to anthranilic acid by acid protonation,
c) recovering said anthranilic acid by precipitation or by dissolving in an organic solvent, and
d) converting said anthranilic acid to aniline by thermal decarboxylation in an organic solvent.

The recombinant bacteria used in said process belong to the family of *Corynebacterium* or *Pseudomonas*. Both bacteria produce o-aminobenzoate at pH 7, under oxic conditions, and typically during the exponential phase. These features of the bacteria described in WO 2015/124687 lead to several problems:
(i) Due to the fermentative production of o-aminobenzoate at pH 7 (step a), a base, e.g. NaOH, need to be added in order to ensure a stable neutral pH. During subsequent step b), an acid, e.g. HCl, needs to be added in order to convert o-aminobenzoate to o-aminobenzoic acid. Therefore, as a by-product, e.g. NaCl is formed. The use of NaOH, HCl, and the waste water treatment of the resulting NaCl salt solution lead to increased production costs of o-aminobenzoic acid produced by the biotechnological process described in the prior art.
(ii) Moreover, o-aminobenzoate is toxic to microbial cells. If microbial cells show increased resistance to o-aminobenzoate, many of the mechanisms underlying said resistance require energy expenditure. Thus, a certain proportion of the fermentable substrate is consumed for maintenance metabolism leading to decreased yields of o-aminobenzoate. For this reason, the high titers of o-aminobenzoate which are required for a reasonable space-time yield of the process concomitantly decrease product yield.
(iii) Since, the fermentation is run under oxic conditions, the fermentation vessel needs to be aerated and stirred, both leading to increased investment and operation costs for the fermentation unit.
(iv) Moreover, o-aminobenzoate is typically produced during the exponential phase and coupled with microbial growth. This fact further decreases the overall yield of o-aminobenzoate production.

Although biotechnological production of o-aminobenzoate from renewable sources as a precursor for aniline production offers potential benefits, all of the above-described factors diminish the potential benefits of this process if bacteria are used in the fermentation.

Therefore, there is a need for alternative methods for producing o-aminobenzoate and aniline from renewable sources.

This problem is solved by the embodiments defined in the claims and the description.

In a first embodiment, the present invention relates to a method for producing o-aminobenzoic acid comprising the steps of
a) fermenting at least one fermentable substrate in a fermentation vessel using a yeast cell capable of converting at least one fermentable substrate into o-aminobenzoic acid; and
b) separating the produced o-aminobenzoic acid from the fermentation broth.

Yeast Cell Capable of Converting a Fermentable Substrate into o-Aminobenzoic Acid A yeast cell capable of converting a fermentable substrate into o-aminobenzoic acid is a yeast cell which converts at least a part of the fermentable substrate into o-aminobenzoic acid and releases at least a part of the produced o-aminobenzoic acid into the fermentation broth. Since o-aminobenzoic acid is an intermediate in the biochemical pathway which leads to the production of the aromatic amino acid tryptophan, wild type yeast cells do not normally release o-aminobenzoic acid. Therefore, the yeast cell capable of converting at least one fermentable substrate into o-aminobenzoic acid is, preferably, a yeast cell whose biochemical pathways are modified in such a way that not all of the produced o-aminobenzoic acid is utilized in further biochemical reactions but accumulates in the cell and is finally released into the fermentation broth.

In principle, there are two approaches to obtain such a cell. (i) The carbon flux through the pathway leading to o-aminobenzoic acid can be increased so that the production rate of o-aminobenzoic exceeds the consumption rate by downstream reactions leading to the synthesis of trypophan.

(ii) The capacity of the pathways which convert o-aminobenzoic acid into subsequent metabolites or products, e.g. tryptophan, can be decreased so that even the production rate of o-aminobenzoic acid found in wild-type strains causes the accumulation of this compound. In a preferred embodiment of the invention at least one biochemical pathway which consumes o-aminobenzoic acid is completely blocked. Particularly advantageous results are obtained if both approaches are combined so that the yeast cell has an increased production rate of o-aminobenzoic acid as compared to a wild-type cell and at the same time a decreased consumption of o-aminobenzoic acid.

Methods for obtaining yeast cells with the above-described properties are well known in the art. Suitable cells may simply be selected by screening for mutants which release o-aminobenzoic acid into the medium. The frequency of mutants in such an experiment may be increased by common means such as ionizing radiation or chemical mutagens. However, as this process depends on chance, the targeting of key enzymes of the relevant pathways by genetic engineering is more preferred. Using common methods of genetic engineering the expression of genes and enzyme activity may be increased, decreased or even abolished at will.

Preferred yeast species to be used in the method of the present invention are *Ashbya gossypii*, *Pichia pastoris*, *Hansenula polymorpha*, *Yarrowia lipolytica*, *Zygosaccharomyces bailii* and *Saccharomyces cerevisiae*. Most preferably, the yeast is *Saccharomyces cerevisiae*.

Preferably, the yeast cell capable of converting a fermentable substrate into o-aminobenzoic acid comprises a modification of anthranilate phosphoribosyltransferase activity which decreases said enzyme activity. By this modification, flux from o-aminobenzoate to N-(5-phospho-D-ribosyl)-anthranilate is decreased or completely abolished. Therefore, said modification leads to the accumulation of o-aminobenzoate.

The term anthranilate phosphoribosyltransferase activity refers to an enzymatic activity which catalyzes the conversion of o-aminobenzoate to N-(5-phospho-D-ribosyl)-anthranilate. In yeast, anthranilate phosphoribosyltransferase activity is mediated by Trp4 (YDR354W).

The above-described decrease of anthranilate phosphoribosyltransferase activity can be achieved by three principle ways: (i) The regulation of the expression of the trp4 gene in yeast can be modified so that transcription of the gene is decreased or abolished. (ii) The nucleic acid sequence of the trp4 gene may be modified so that the enzyme encoded by the modified gene has a lower specific activity. (iii) The trp4 gene can be replaced by gene derived from an organism other than yeast and encoding an enzyme with a lower specific anthranilate phosphoribosyltransferase activity than Trp4.

In an especially preferred embodiment of the present invention, the yeast cell has no residual anthranilate phosphoribosyltransferase activity. Preferably, this is achieved by abolishing the expression of the trp4 gene in the yeast cell or by modifying the nucleic acid sequence of the trp4 gene in such a way that a protein without anthranilate phosphoribosyltransferase activity results. A strain resulting from such modification is also known in the art as "knock-out strain". Obviously, such a strain is auxotrophic for L-tryptophan.

O-Aminobenzoic Acid

The term "o-aminobenzoic acid" as referred to in the present application relates to 2-aminobenzoic acid. This compound is also known as anthranilic acid. The person skilled in the art knows that an acid may be present in its protonated form as neutral substance or deprotonated as anion. In aqueous solution a part of the acid is protonated and a part is present as anion. The ratio between protonated acid and anion depends on the pH of the solution and the dissociation constant K, of the acid in question. Unless indicated otherwise, the term "o-aminobenzoic acid" as used in this application always refers to both the protonated acid as well as the corresponding anion.

Fermentation Broth

At the beginning of the fermentation, the fermentation broth comprises the recombinant yeast cells and at least one fermentable substrate. Preferably, the fermentation broth additionally comprises at least one compound selected from the group consisting of buffer systems, inorganic nutrients, amino acids, vitamins and other organic compounds essential for growth and/or maintenance of the recombinant yeast cell. The fermentation broth is water-based. After a sufficient time of fermentation the fermentation broth also comprises o-aminobenzoic acid, the desired fermentation product.

Fermentable Substrate

A fermentable substrate as understood by the present application is any organic compound or mixture of organic compounds which can be utilized by the recombinant yeast cell to produce o-aminobenzoic acid in the presence or absence of oxygen. Since a preferred embodiment of the method of the present invention relates to the production of o-aminobenzoic acid under anoxic conditions, the fermentable substrate is preferably an organic compound or mixture of organic compounds which can be converted under anoxic conditions to o-aminobenzoic acid. Preferred fermentable substrates additionally serve as energy and carbon sources for the growth of the recombinant yeast cells. Preferred fermentable substrates are processed sugar beet, sugar cane, starch-containing plants and lignocellulose. Also preferred as fermentable substrate are glycerol and C1-compounds, preferably CO, and fermentable sugars.

Preferred fermentable sugars are C-5 monosaccharides, C-6 monosaccharides, disaccharides, and tri-saccharides. Preferred C-5 monosaccharides are xylose and arabinose. Preferred C-6 monosaccharides are glucose, fructose and mannose. A preferred disaccharide is saccharose and a preferred trisaccharide is kestose. Preferred starch-containing plants are corn, wheat and rye. Lignocellulose is preferably selected from the group consisting of straw, wood and bagasse.

Fermentation Broth, Other Constituents

In addition to the fermentable substrate, the fermentation broth also comprises inorganic nutrients, amino acids, vitamins and other organic compounds which are required for growth and/or maintenance metabolism of the recombinant yeast cell. The person skilled in the art knows the types and amounts of inorganic nutrients which must be supplied to the medium in order to achieve the desired biomass concentration. Different strains of yeast may differ with respect to their need for vitamins, amino acids and other organic compounds. If this information is not given by the supplier of the strain, it may be gained by simple growth experiments which are routine to the person skilled in the art.

The genetic modification of the yeast cell which renders it capable of accumulating and releasing o-aminobenzoic acid may interrupt or decrease the carbon flux through biochemical pathways which provide organic compounds essential for growth and/or maintenance of the recombinant yeast cell. Recombinant yeast cells with such genetic modifications have, therefore, particular auxotrophies. The composition of the medium must take into account such auxotrophies. If the yeast cell has no anthranilate phosphoribosyltransferase activity as in a preferred embodiment of the present invention, it is auxotrophic for L-tryptophan and this amino acid has to be added to the fermentation broth.

Preferably, the fermentation broth additionally comprises at least one buffer system. The buffer system comprises a weak acid and its conjugate base or vice versa. As an effect of the buffer, addition of a strong acid or base to the fermentation broth changes its pH value considerably less than in the absence of a buffer. For each desired pH range there is at least one suitable buffer system. Such buffers are known to the person skilled in the art. One preferred buffer is a citrate buffer.

However, in an industrial application of the method of the present invention it will be preferred to adjust the pH by adding an acid or a base to the fermentation broth as buffer substances cause additional cost.

Fermentation Vessel

The term "fermentation vessel" relates to any vessel which can be used to conduct the fermentation of the fermentable substrate to o-aminobenzoic acid. Preferably, said fermentation vessel comprises means for measuring relevant process parameters such as temperature, pH, substrate concentration, product concentration, dissolved oxygen and cell density of the fermentation broth. Preferably, the fermentation vessel additionally comprises means to adjust at least one of said process parameters.

Generally, the person skilled in the art knows how to design fermentation vessels which are suitable for a given fermentation process. Particularly, the design of the fermentation vessel must be adapted to the desired mode of the fermentation process (batch, fed batch or continuous fermentation). Fermentation vessels include stirred tank reactors, membrane reactors, plug flow reactors, or loop reactors (Bioprozesstechnik, Horst Chmiel, ISBN-10: 3827424763, Spektrum Akademischer Verlag). Preferred reactor vessels for aerobic and anaerobic fermentation are stirred tank reactors or loop reactors (especially airlift).

The present invention relates to an integrated process of producing o-aminobenzoic acid in method step a) and separating the produced o-aminobenzoic acid in method step b). The present applications discloses several ways of performing method step b). Some of these require specialized fermentation vessels. Such particularly preferred vessels are described further below in connection to the separation step b).

Batch/Fed Batch/Continuous Culture

There are three principle modes of performing a fermentation: batch, fed batch and continuous fermentation.

In a batch fermentation a fermentation broth comprising recombinant yeast cells, at least one fermentable substrate and further required components as described above is prepared. The fermentation broth is then incubated in a fermentation vessel under conditions which are suitable for the recombinant yeast cells to produce o-aminobenzoic acid. A batch fermentation may also involve growth of the biomass. However, it is in principle possible to incubate the recombinant yeast cells under conditions which do not allow growth because the product formation in the recombinant yeast cells of the present invention is not coupled with growth. During the fermentation no additional fermentable substrate is added. However, it may be advantageous to add inorganic acids or bases to the fermentation broth in order to maintain or achieve a desired pH value. Once the concentration of the fermentable substrate falls below a defined level, a certain amount of o-aminobenzoic acid is produced or the production rate of o-aminobenzoic acid falls below a defined level, the fermentation is stopped and the o-aminobenzoic acid is separated from the fermentation broth.

In a fed batch fermentation a fermentation broth comprising recombinant yeast cells, at least one fermentable substrate and further required components as described above is prepared. The fermentation broth is then incubated in a fermentation vessel under conditions which are suitable for the recombinant yeast cells to produce o-aminobenzoic acid. A fed batch fermentation may also involve growth of the biomass. After the start of the fermentation additional fermentable substrate is added at least once to the fermentation broth. Thus, a typical fed batch fermentation is characterized by a period of biomass growth and/or product formation until the concentration of the fermentable substrate drops below a certain threshold. Once this happens, additional fermentable substrate is added and the fermentation resumes. This process can be repeated several times. In the method of the present invention it is preferably repeated at least once, at least twice, at least three times or at least four times. After the desired number of repetitions, the o-aminobenzoic acid is separated from the fermentation broth. Compounds other than the fermentable substrate, particularly inorganic acids or bases, may be added as often as required.

In a continuous fermentation the fermentable substrate is added continuously to the fermentation broth. Typically, fermentation broth comprising yeast cells and optionally o-aminobenzoic acid is continuously removed from the fermentation vessel and replaced by fresh fermentation broth. In a typical continuous fermentation, concentrations of biomass, fermentable product and o-aminobenzoic acid are in a steady state. The yeast cells in such a system never reach their stationary growth phase because cells are continuously removed and the addition of fresh fermentation broth and fermentable substrate maintains conditions which allow cell proliferation. If cells are removed from the product stream and re-fed to the continuously operated fermentation vessel, substrate consumption for cell proliferation can be reduced.

The total fermentation capacity can be divided between several fermenters, and break tanks can be used to enable a continuous supply of fermentation material to the downstream section comprising steps.

Anoxic Conditions

"Anoxic conditions" as referred to in the present application are conditions characterized by lower oxygen saturation of the fermentation broth than would be present without oxygen consumption in the medium at the oxygen partial pressure present in the fermentation vessel. Anoxic conditions prevail in the fermentation broth if oxygen consumption of the yeast cells exceeds the transport rate of oxygen from the air into the fermentation broth. This imbalance between oxygen supply and consumption results in a decreasing oxygen concentration in the fermentation broth. Since yeast is able to live and even grow anaerobically, anoxic conditions in the fermentation broth are acceptable. Therefore, the fermentation vessel does not necessarily need to be equipped with aeration devices resulting in a simpler and cheaper apparatus.

To ensure sufficient growth under anoxic conditions at least very little amounts of oxygen must be supplied to support enzyme reactions that are essential for growth and depend on the presence of oxygen, e.g. mono oxygenases involved in ergostyrol biosynthesis.

Preferably, the term "anoxic conditions" refers to 5 to 90%, more preferably 5 to 80%, even more preferably 5 to 60% and most preferably 5 to 40% of the oxygen saturation which would be present in the fermentation broth under atmospheric oxygen partial pressure at the given temperature without oxygen consumption.

Production During Stationary Growth Phase

It has been surprisingly found in the study underlying the present invention that production of o-aminobenzoic acid by yeast is not coupled with growth. Therefore, in a preferred embodiment of the method of the present invention a considerably amount of the o-aminobenzoic acid produced in method step a) is produced during the stationary growth phase. This feature of yeast is preferably utilized in batch or fed batch fermentations, which can be adapted to last during the stationary growth phase of the cells. Furthermore, the ability of yeast to produce o-aminobenzoic acid during the stationary growth phase makes it possible to recycle yeast cells separated from the fermentation for further fermentations. Generally, the decoupling of biomass growth and product formation in yeast cells leads to a more economical utilization of the substrate because less substrate is consumed for the buildup of biomass and, thus, a greater proportion is channeled into production of o-aminobenzoic acid.

The term "stationary growth phase" as referred to in the present application is a phase during cultivation characterized by a steadiness in biomass, i.e. neither increase nor decrease of the biomass, which can be triggered by fermentation conditions or is based on capacity limits of nutrient(s) and/or space. It is preceded by a growth phase. Preferably, biomass during the stationary growth phase does not change by cell proliferation or cell death by more than 30%, more preferably not more than 20% and most preferably not more than 10% per 5 hours.

pH of the Process

Yeast is able to grow at pH-values below 7.0. Hence, method step a) is preferably performed at an acidic pH, i.e. a pH of less than 7.0. It is preferred to perform method step a) at the lowest possible pH which is close to the isoelectric point of aminobenzoic acid and still allows for growth of the yeast cells or at least o-aminobenzoic production during the stationary growth phase. Since the proportion of o-aminobenzoic acid which is present in the protonated neutral form increases with decreasing pH, the solubility of o-aminobenzoic acid decreases with pH with a solubility minimum at the isoelectric point of o-aminobenzoic acid. Lower concentrations of dissolved o-aminobenzoic acid in the fermentation broth mean less toxicity to the yeast cells. Moreover, a larger proportion of protonated neutral o-aminobenzoic acid with low solubility in water facilitates its separation from the fermentation broth in method step b).

The pH value during method step a) ranges preferably from 2.0 to 6.0, even more preferably from 2.5 to 5.5, even more preferably from 3.0 to 5.5 and most preferably from 3.5 to 4.0.

In one preferred embodiment of the method of the present invention, crystals of o-aminobenzoic acid are added to the fermentation broth as crystal seeds in order to facilitate crystallization. Preferably, the crystals are added in the latter half, last third or last quarter of a batch fermentation. Also preferably, the crystals are added in the latter half, last third or last quarter of a fed batch fermentation. The crystals of o-aminobenzoic acid may be obtained from commercial suppliers or may be a product of an earlier production run of the method of the present invention.

Separation of o-Aminobenzoic Acid from the Fermentation Broth

Any method for the separation of solid particles from a liquid phase may be used in method step b). Preferred methods are filtration, settling, hydrocyclons and centrifugation. Since protonated o-aminobenzoic acid is better soluble in organic solvents such as dodecanol, undecylamine, dicyclohexylamine, 2,6-diethylaniline, butanic acid octylester, acetic acid dodecylester, dimetyhlphthalate, benzylhexylether, diethylelgylkol di-n-butylether than in water, extraction of o-aminobenzoic acid with one or more of the aforementioned solvents is another preferred embodiment of method step b).

Figure 7:
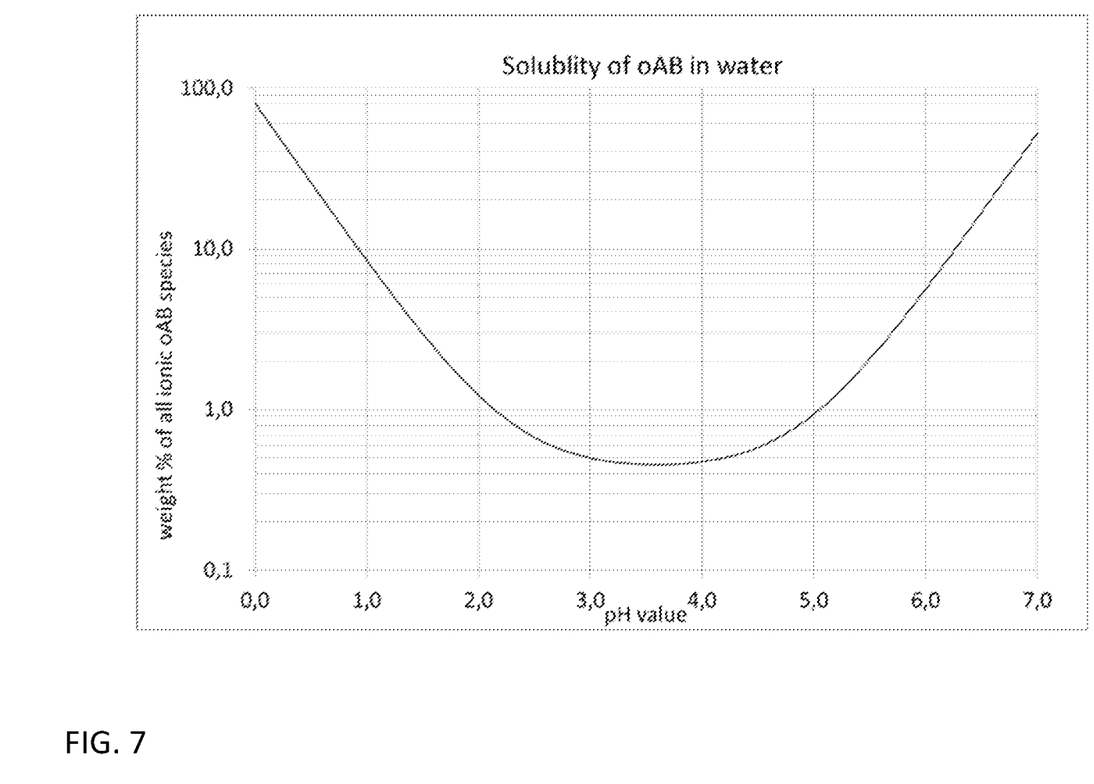
FIG. 7: Diagram showing the solubility of oAB in water depending on the pH. It can be seen that solubility reaches its minimum between pH 3 and pH 4.

Because the solubility of o-aminobenzoic acid in water decreases with pH, it is preferred to perform the separation at a pH below 7.0. Preferably, in method step b) the pH is below 6.0, more preferably below 5.0 and most preferably between 3.4 and 4.0. If the pH value is decreased before or during method step b), the use of strong mineral acids such as HCl or $H_3PO_4$ is preferred. As shown in FIG. 7, the solubility of ortho-aminobenzoic acid (oAB) in water is particularly low in the range between pH 3.0 and pH 4.0. Hence this range is also preferred.

The fermentation broth may be acidified at any point of time before or during the separation step b). However, due to the inherent acid tolerance of yeast cells it is preferred to perform the complete fermentation process including method steps a) and b) at a pH between 3.0 and 5.0, more preferably between pH 3.0 and 4.0 and most preferably between pH 3.4 and 4.0.

In a preferred embodiment of the invention, the pH is stabilized in the range defined above by substoichiometric addition of an alkaline buffer. In a more preferred embodiment the pH is stabilized in the range defined above without the use of a buffer system.

If the fermentation in method step a) is performed at a pH between 3.0 and 4.0, it is preferred that method step b) is performed at the same pH without further acidification because the solubility of o-aminobenzoic acid in water in this pH-range is sufficiently low.

In the fermentation broth, two types of particles are present: crystals of o-aminobenzoic acid and yeast cells.

In one preferred embodiment, the crystalized o-aminobenzoic acid is separated from the fermentation broth without separating the yeast cells from the fermentation broth. Most preferably, this is achieved by methods which utilize the different density of yeast cells and crystalized o-aminobenzoic acid. The rotation speed of the stirrer in the fermentation vessel can be adjusted so that only the yeast cells are kept in suspension while the crystallized oAB which has a higher density than the yeast cells settles at the bottom of the fermentation vessel. The settled solid oAB can then be removed and processed further, e.g. by filtration and drying. Thus, the separation of oAB from yeast cells and fermentation broth can be performed without removing fermentation broth from the fermentation vessel.

Density of the yeast is in the range of 1.08-1.1 $g/cm^3$ depending on the cell cycle. Density of bulk oAB is 1.41 $g/cm^3$. The particle size is also an influential parameter. The yeast cells have a size distribution that corresponds to characteristic length below 10 micrometers. A typical size distribution for yeast cells can be found in literature (P. Jorgensen et al. Science 297: 395, 2002).

Differences in size and density lead to difference in settling/floating velocity as can be represented for the simplified case of Stokes law via the following equation:

$$v_s = \frac{g(\rho_s - \rho_l)d_p^2}{18\,\mu}$$ Equation 1

$v_s$ the settling velocity $g$ acceleration of gravity $\mu$ viscosity of the liquid medium $\rho_s$ solid density $\rho_l$ liquid density $d_p$ particle diameter For a stirred system the minimum rotation speed to suspend a particle also depends on the size and density of the particle as represented with the Zwietering equation; according to which the ratio between the rotation speed to suspend two particles with different densities and sizes can be represented as in $$\frac{rps_c}{rps_y} = \left[\frac{\rho_c - \rho_l}{\rho_y - \rho_l}\right]^{0.45}\left(\frac{d_{pc}}{d_{py}}\right)^{0.2}$$ Equation 2

Figure 3:
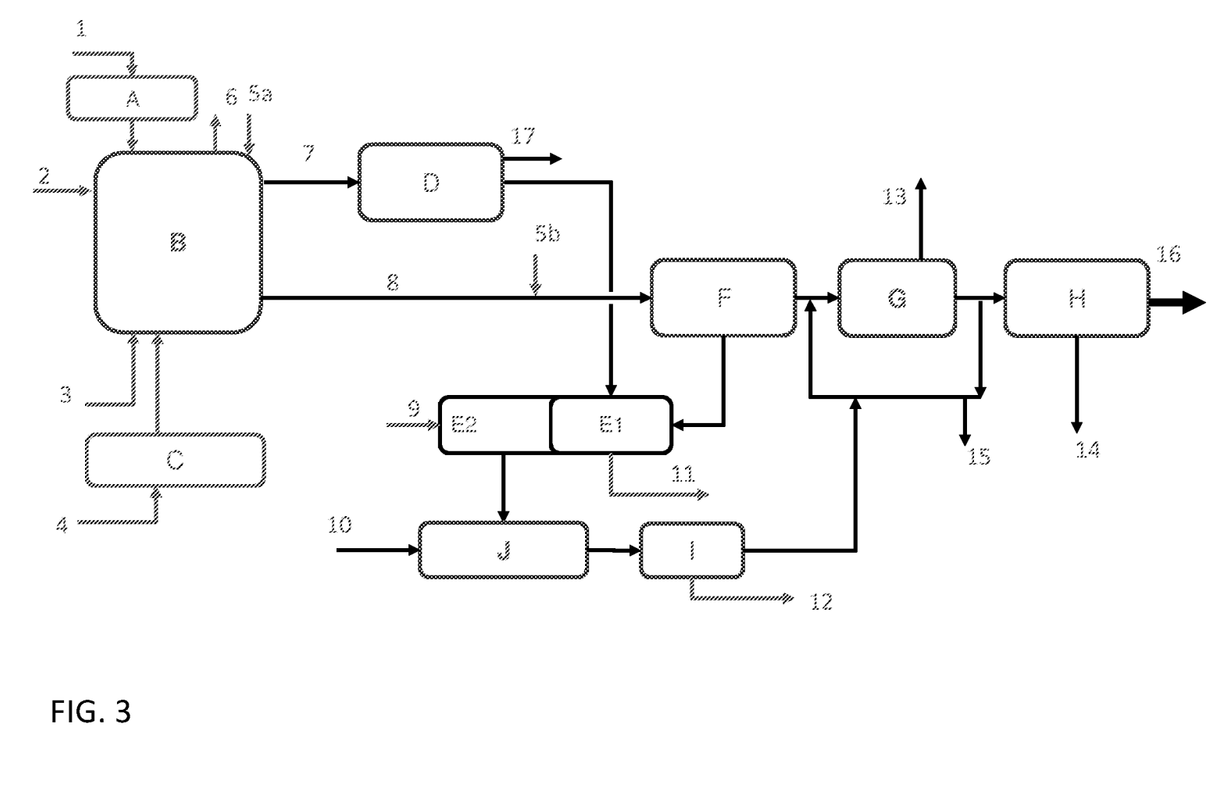

$rps_c$ the critical rotation speed for the crystals $rps_y$ the critical rotation speed for the yeast $\rho_c$ crystals density $\rho_y$ yeast density $\rho_l$ liquid density $d_{pc}$ crystals diameter $d_{py}$ yeast diameter A preferred process for separating oAB from the fermentation broth in method step b) is based on these phenomena. A schematic depiction of this embodiment is depicted in FIG. 3. Nascent oAB crystals in the fermenter are given sufficient time to grow to sizes above a given size, preferably above 100 micron, most preferably above 500 microns. The size is selected by defining the cut off radius of the filter used in the filtration F downstream of the fermenter. Attaining such sizes facilitates (i) their separation from the cells and (ii) dewatering of oAB for further processing.

The filtrate can be recycled to the fermentation vessel, to allow for more residence time and to introduce an elutriation effect. The rotation speed of the stirrer is adjusted so that it is above the minimum speed to keep the yeast cells suspended while below the minimum speed to keep the crystals with the selected cut off size suspended. The ratios of minimum suspension speeds for various combinations of size and density are given in Table 1, which shows that a wide range of rotation speeds exist to satisfy this criterion.

TABLE 1

| $\rho_c$ | | | 1410 | kg/m³ |
| $\rho_y$ | | | 1080 | kg/m³ |

| $d_{py}$ microns | $d_{pc}$ microns | $\rho_l$ Kg/m³ | ratios of minimum suspension speeds $rps_c/rps_y$ |
|---|---|---|---|
| 5  | 100 | 1000 | 4 |
| 40 | 100 | 1010 | 3 |
| 5  | 500 | 1020 | 6 |
| 40 | 500 | 1030 | 4 |
| 5  | 200 | 1040 | 6 |
| 40 | 200 | 1050 | 4 |

This recovery process can be run in parallel with the fermentation or in a harvesting step subsequent to fermentation. In a preferred embodiment of the present invention, said harvesting step is conducted at lower pH values, preferably below 5.0, more preferably between pH 3.0 and 4.0, most preferably between pH 3.4 and 4.0 to maximize the recovery of oAB crystals. Fermentation and harvesting can be operated in a continuous, semi-batch or batch operation modes. In an especially preferred embodiment of the invention, the above-described method of separation is used in combination with a continuous fermentation mode.

If the fermentation is performed as a batch or fed batch process, it is preferred to isolate the solid oAB formed during the fermentation process as described above and to isolate the soluble oAB remaining in the fermentation broth at the end of the fermentation by adsorption and desorption as described further below in this application.

In another preferred embodiment of the present invention, both o-aminobenzoic acid and yeast cells are separated from the fermentation broth in a single step or in two separate steps. If yeast cells and o-aminobenzoic acid are separated from the fermentation broth in one step, it is preferred to add a further step of separating o-aminobenzoic acid from yeast cells to the method. In this embodiment, the separation is performed outside of the fermentation vessel, i.e. the fermentation broth containing yeast cells and oAB is removed from the fermentation vessel and subjected to separation of oAB from the yeast cells and the liquid constituents of the fermentation broth.

Figure 4:
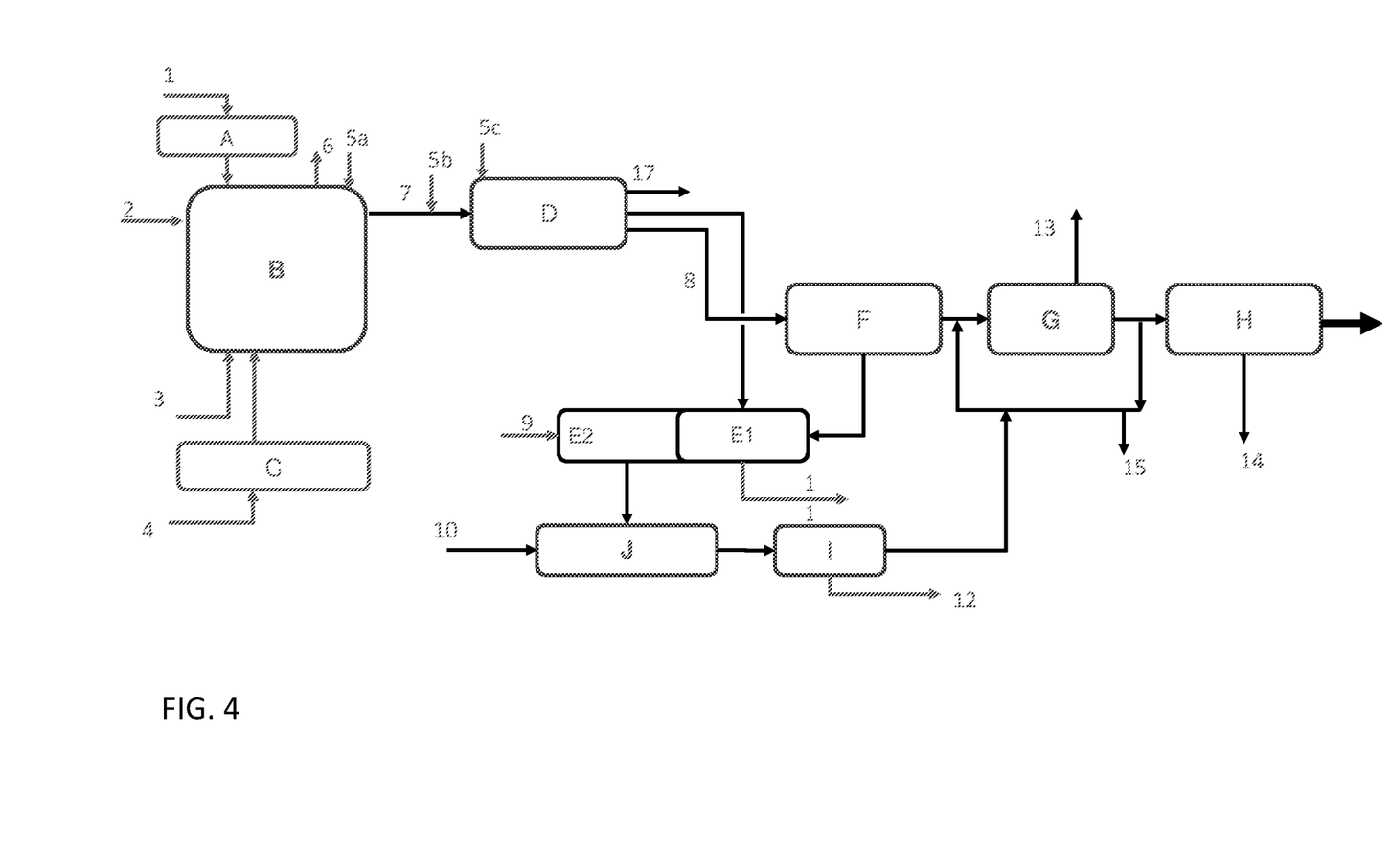

For this purpose any unit operation based on differences in particle movement in flow, gravitational or centrifugal field, can be implemented. For example, settling basins, centrifuges, hydrocyclones, etc. filtration can be also designed, as for example in Perry's Chemical Engineers' Handbook, Eighth Edition FIG. 4 depicts the process schematically. Fermentation broth comprising yeast cells and oAB is removed from the fermentation process B and subjected to a separation D which employs at least one of the means described above. In order to recover further oAB which is dissolved in the fermentation broth and cannot be separated by the above-described means and methods, the fermentation broth may be subjected to a further step of adsorption and desorption E. Alternatively, the fermentation broth resulting from separation D may be fed back into the fermentation vessel.

Even at the solubility minimum of oAB at a pH between pH 3.0 and pH 4.0, approximately 5 g/l oAB remain dissolved in the fermentation broth. Solid oAB is only formed if higher oAB concentrations are present. Thus, methods of solid/liquid separation cannot be used to recover oAB at concentrations below 5.0 g/l, thus leading to a potential loss of oAB in discarded fermentation broth. In order to recover the dissolved oAB, adsorption to a suitable solid phase followed by desorption is an isolation method which can be used alone or in combination with other methods in various embodiments of the present invention.

In any embodiment of method step b) which results in the separation of yeast cells from the fermentation broth by liquid/solid or solid/solid/liquid separation, it is preferred to return at least a part of the separated yeast cells to the original fermentation broth or to add them to fresh fermentation broth. Since yeast cells are able to produce o-aminobenzoic decoupled from biomass growth, existing yeast cells can be used in further fermentations without the need to expend substrate for the production of new biomass.

In a further preferred embodiment of method step b) of the present invention, the separation of oAB from the yeast cells and the fermentation broth in method step b) is performed by extraction with a suitable solvent. This process is also referred to as liquid extraction of oAB.

Suitable solvents are those which are non-soluble in water, have a large density difference with water and have a melting point below 25° C. Preferably, a suitable solvent additionally has a boiling point higher than aniline. Preferred solvents are dodecanol, undecylamine, dicyclohexylamine, 2,6-diethylamine, butanic acid octylester, acetic acid dodecylester, benzyl hexyl ether, diethylene glycol, di-n-butyl ether. Especially preferred is dodecanol.

In one preferred embodiment of the extraction process, extraction is performed by adding the solvent to the fermenting vessel. The solvent can be continuously added to and removed from the fermentation vessel so that a constant amount of solvent is always present. Because solvent which carries dissolved oAB is continuously replaced by fresh solvent, the solvent which is present in the fermentation vessel is never saturated with oAB, thus keeping oAB levels in the aqueous phase low. This mitigates the problem of toxicity of oAB towards yeast cells. However, the yeast cells need to be able to tolerate the used solvent. This embodiment is particularly suited to a continuous fermentation process.

Figure 5:
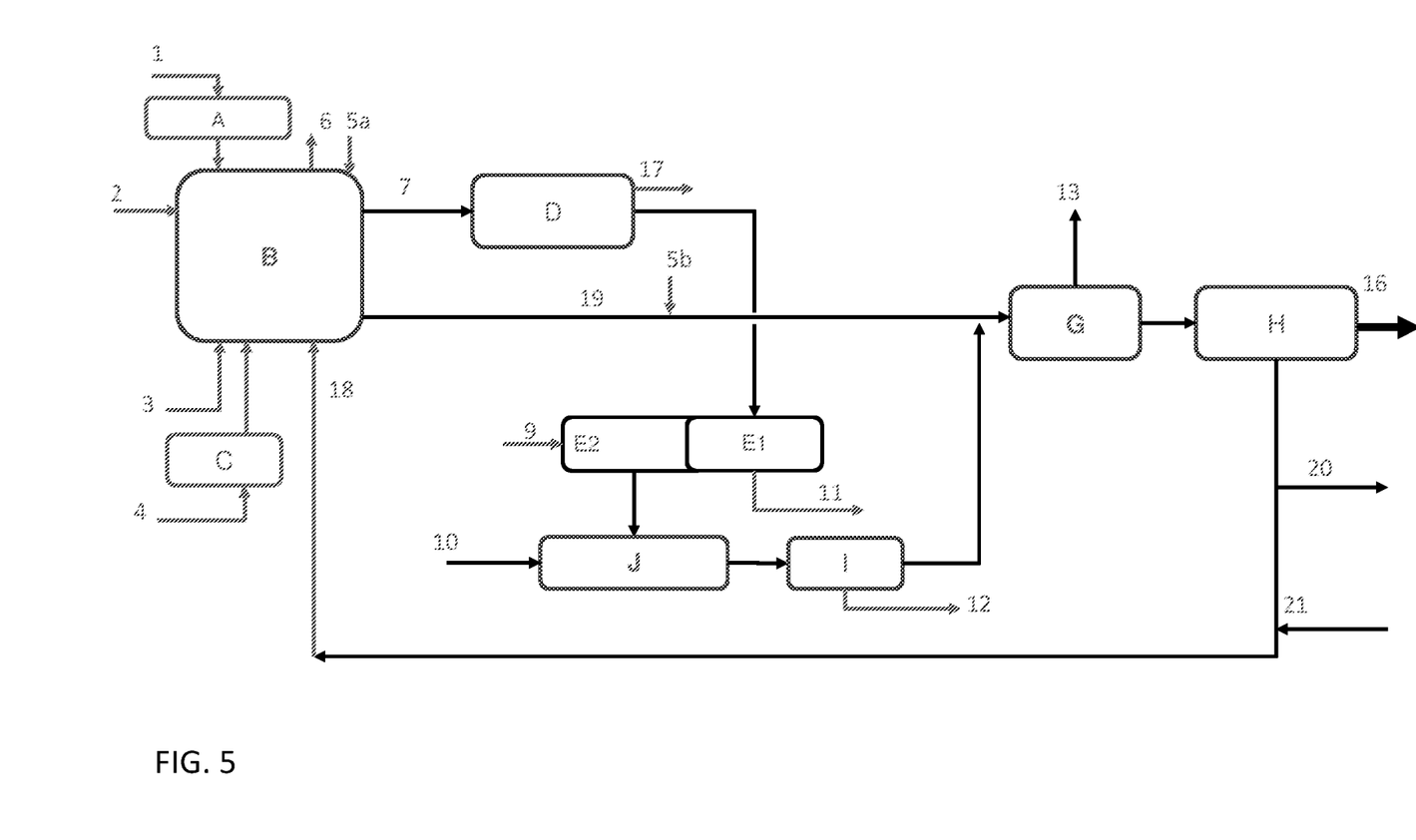

This process is schematically depicted in FIG. 5. The oAB carrying solvent is removed from the fermentation B via stream 19 and subjected to decarboxylation G. Optionally, in a fed-batch or continuous process, fermentation broth without solvent is removed from the fermentation via stream 7 and subjected to liquid/solid separation in order to obtain pure fermentation broth. Said pure fermentation broth is preferably subjected to adsorption and desorption E in order to recover oAB which remains dissolved in the aqueous phase.

In another preferred embodiment of the extraction process, the solvent is added to fermentation broth which has been removed from the fermentation vessel. The yeast cells may be removed from the fermentation broth before the solvent is added. However, it is equally preferred to perform the liquid extraction of oAB with the fermentation broth including the yeast cells.

Figure 6:
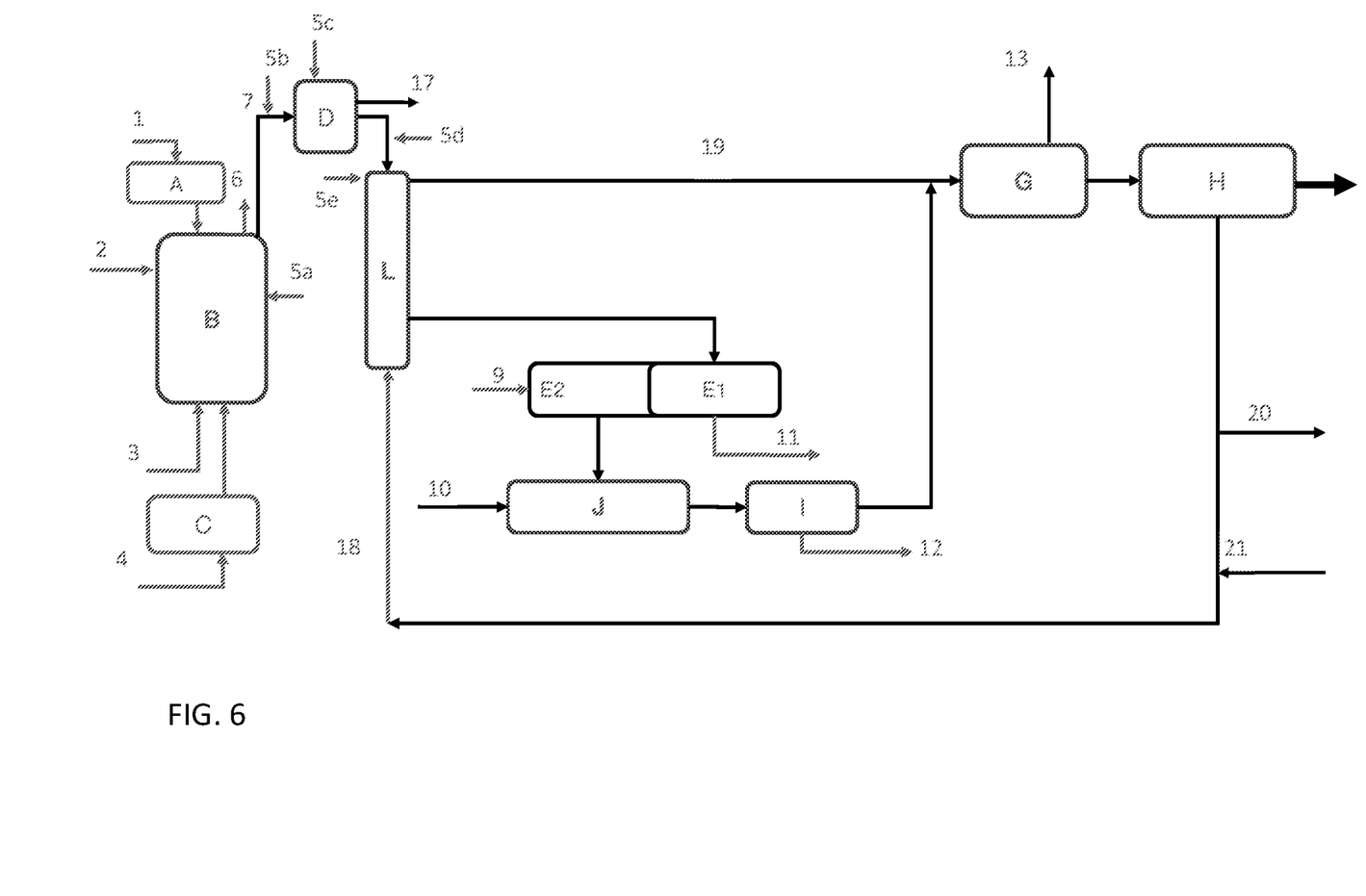

A preferred embodiment of this process is schematically depicted in FIG. 6. Fermentation broth containing yeast cells and oAB is removed from the fermentation B. The biomass (stream 17) is separated from the liquid phase and the liquid phase is subjected to liquid extraction L. The aqueous phase resulting from liquid extraction, i.e. the fermentation broth without cells and with a residual amount of dissolved oAB, is preferably subjected to adsorption and desorption E in order to recover the residual oAB. It should be noted that the separation of biomass D may also be omitted so that the complete fermentation broth is subjected to liquid extraction.

The use of yeast instead of aerobic bacteria for the production of o-aminobenzoic acid from fermentable substrates has several advantages:

(i) Yeast survives and even proliferates under anoxic conditions. Thus, decreased oxygen concentrations during the fermentation process do not decrease product yield so that means for aeration of the fermentation broth may be omitted or reduced. This decreases cost and complexity of the fermentation vessel.

(ii) Yeast survives and even proliferates under acid conditions. This decreases solubility of o-aminobenzoic acid in water so the cells are exposed to lower concentrations of dissolved o-aminobenzoic acid than at neutral pH. This mitigates the problem of product toxicity. Furthermore, the amount of base that has to be added in order to keep the pH of the fermentation broth stable is lower, thus decreasing the amount of salt produced in the process.

(iii) If the method is performed at acidic pH which is only possible with yeast, separation step b) is facilitated. Since the solubility of o-aminobenzoic acid decreases with pH, less or even no acid must be added before method step b), thus further decreasing the amount of salt produced by the method. Moreover, if sufficient product concentrations are reached, crystalized o-aminobenzoic acid forms during fermentation step a) and can be removed from the fermentation broth while fermentation step a) continues. This allows the integration of yeast-based fermentations in several advantageous process concepts described further below in this application.

(iv) It has been surprisingly found that formation of o-aminobenzoic acid by yeast is not coupled to biomass growth and, hence, continues with acceptable rates during the stationary growth phase. Process concepts which involve the use of yeast cells during the stationary growth phase have the advantage that a lower proportion of the fermentable substrate is diverted into biomass growth as compared to process concepts which use cells only in the exponential growth phase. This is a particular advantage of the method of the present invention over bacteria-based methods known from the prior art.

In one preferred embodiment, the present invention relates to the further processing of the o-aminobenzoic acid produced according to the method described above to aniline. Thus, the present invention relates to a method for producing o-aminobenzoic acid or aniline, wherein o-aminobenzoic acid is produced as set forth above in this application and the conversion of o-aminobenzoic acid to aniline is conducted by the further method steps defined below.

Preferably, o-aminobenzoic acid is converted to aniline by purely chemical methods, i.e. without the use of microorganisms or enzymes as catalysts. A preferred chemical method is thermal decarboxylation of o-aminobenzoic acid.

Thermal decarboxylation is preferably performed in the presence of a catalyst. A catalyst is a zeolite catalyst, wherein said zeolite catalyst most preferably is zeolite H-Y (e.g. as obtained from Zeolyst International, catalog number CBV600). The acid catalyst zeolite H-Y ($SiO_2/Al_2O_3$ can be between 5 and 7, preferably it is 5.5) has a particularly high acidic character and has a wider pore size (0.7-0.8 nm) than e.g. ZSM5-27 (e.g. as obtained from Clariant SuedChemie, catalog number MFI-27, SiO2/Al2O3=27), which also possesses a strong acidic character, but which has smaller pore size (0.5 nm) so that o-aminobenzoic acid molecules cannot effectively penetrate into them and consequently do not have easy access to the active sites of the acidic catalyst, thereby reducing its effectivity.

Preferably, thermal decarboxylation is performed in an organic solvent. O-aminobenzoic acid, e.g. in the form of crystals, with or without residual moisture, is thermally decarboxylated, preferably by feeding the acid to a decarboxylation reactor. The thermal decarboxylation can be performed at a temperature between 150° C. and 250° C., preferably between 160° C. and 220° C., more preferably between 180° C. and 200° C. The thermal decarboxylation can be run for sufficient time to react o-aminobenzoic acid to aniline. Preferably, thermal decarboxylation is run for 0.5 hours to 3 hours.

Thermal decarboxylation can be performed in the presence of an acid catalyst in order to speed up the thermal decarboxylation.

Thermal decarboxylation can be run in a solvent such as water, aniline, or in 1-dodecanol, preferably in 1-dodecanol, or in a mixture of 1-dodecanol and aniline.

Further, thermal decarboxylation can be performed in a reactor, wherein the pressure in the reactor can be selected as a function of how much of the liquid phase is allowed to evaporate during the reaction and leave the reactor with the carbon dioxide ($CO_2$) that is a product of the decarboxylation.

In a further embodiment of the method according to the invention, the thermal decarboxylation is followed by a further step of purifying the aniline, preferably by distillation.

In another embodiment, the present invention relates to a recombinant yeast cell which comprises a modification of anthranilate phosphoribosyltransferase activity which decreases said enzyme activity.

Preferred yeast species to be used in the method of the present invention are *Ashbya gossypii*, *Pichia pastoris*, *Hansenula polymorpha*, *Yarrowia lipolytica*, *Zygosaccharomyces bailii* and *Saccharomyces cerevisiae*. Most preferably, the yeast is *Saccharomyces cerevisiae*.

The term anthranilate phosphoribosyltransferase activity refers to an enzymatic activity which catalyzes the conversion of o-aminobenzoate to N-(5-phospho-D-ribosyl)-anthranilate. In a preferred embodiment of the present invention, anthranilate phosphoribosyltransferase activity is mediated by Trp4 (YDR354W).

The above-described decrease of anthranilate phosphoribosyltransferase activity can be achieved by three principle ways: (i) The regulation of the expression of the trp4 gene in yeast can be modified so that transcription of the gene is decreased or abolished. (ii) The nucleic acid sequence of the trp4 gene may be modified so that the enzyme encoded by the modified gene has a lower specific activity. (iii) The trp4 gene can be replaced by gene derived from an organism other than yeast and having a lower specific anthranilate phosphoribosyltransferase activity than Trp4.

In an especially preferred embodiment of the present invention, the yeast cell has no residual anthranilate phosphoribosyltransferase activity. Preferably, this is achieved by abolishing the expression of the trp4 gene in the yeast cell or by modifying the nucleic acid sequence of the trp4 gene in such a way that a protein without anthranilate phosphoribosyltransferase activity results. A strain resulting from such modification is also known in the art as "knock-out strain". Obviously, such a strain is auxotrophic for L-tryptophan.

The recombinant yeast cell may comprise further genetic modifications which increase the availability of precursors for synthesis of o-aminobenzoic acid.

In yet another embodiment, the present invention relates to the use of the recombinant yeast cell for producing o-aminobenzoic acid from at least one fermentable substrate.

In a particularly preferred embodiment of the present invention, the recombinant yeast cell is used in the method described above.

BRIEF DESCRIPTION OF THE FIGURES

FIG. 3: Schematic depiction of the separation of solid oAB in the fermenting vessel. A: sterilization; B: fermentation; C: air compression; D: biomass separation; E1 and E2: adsorption and desorption; F: filtration; G: decarboxylation; H: distillation; I: filtration; J: crystallization.
- 1: carbon source (e.g. sugar); 2: nitrogen sources (e.g. $NH_3$); 3: buffer solution (e.g. NaOH); 4: air; 5A and 5B: feeding points for HCl, may be used alternatively or combined; 6: exhaust air; 7: biomass suspension; 8: oAB crystals suspension; 9: eluent, e.g., dilute NaOH; 10: HCl; 11: waste water; 12: waste water; 13: $CO_2$; 14: residue; 15: residue; 16: aniline product; 17: biomass FIG. 4: Schematic depiction of the separation of solid oAB from the fermentation broth outside of the fermentation vessel. A: sterilization; B: fermentation; C: air compression; D: solid/solid/liquid separation; E1 and E2: adsorption and desorption; F: filtration; G: decarboxylation; H: distillation; I: filtration; J: crystallization.
- 1: carbon source (e.g. sugar); 2: nitrogen sources (e.g. $NH_3$); 3: buffer solution (e.g. NaOH); 4: air; 5A and 5B and 5C: feeding points for HCl, may be used alternatively or combined; 6: exhaust air; 7: fermentation broth (biomass, water, oAB); 8: oAB crystals suspension; 9: eluent, e.g., dilute NaOH; 10: HCl; 11: waste water; 12: waste water; 13: $CO_2$; 14: residue; 15: residue; 16: aniline product; 17: biomass FIG. 5: Schematic depiction of the liquid extraction of oAB performed inside the fermentation vessel. A: sterilization; B: fermentation; C: air compression; D: biomass separation; E1 and E2: adsorption and desorption; G: decarboxylation; H: distillation; I: filtration; J: crystallization.
- 1: carbon source (e.g. sugar); 2: nitrogen sources (e.g. $NH_3$); 3: buffer solution (e.g. NaOH); 4: air; 5A and 5B: feeding points for HCl, may be used alternatively or combined 6: exhaust air; 7: biomass suspension; 9: eluent, e.g., dilute NaOH; 10: HCl; 11: waste water; 12: waste water; 13: $CO_2$; 16: aniline product; 17: biomass; 18: solvent; 19: oAB solution in solvent to feed to reaction; 20: solvent purge; 21: solvent makeup.

FIG. 6: Schematic depiction of the liquid extraction of oAB performed outside of the fermentation vessel. A: sterilization; B: fermentation; C: air compression; D: biomass separation; E1 and E2: adsorption and desorption; G: decarboxylation; H: distillation; I: filtration; J: crystallization; L: liquid extraction.
- 1: carbon source (e.g. sugar); 2: nitrogen sources (e.g. $NH_3$); 3: buffer solution (e.g. NaOH); 4: air; 5A and 5B and 5C and 5D and 5E: feeding points for HCl, may be used alternatively or combined 6: exhaust air; 7: fermentation broth (biomass, water, oAB); 9: eluent, e.g., dilute NaOH; 10: HCl; 11: waste water; 12: waste water; 13: $CO_2$; 16: aniline product; 17: biomass; 18:

solvent feed to extractor; 19: oAB solution in solvent to feed to reaction; 20: solvent purge; 21: solvent makeup

The following examples are only intended to illustrate the invention. They shall not limit the scope of the claims in any way.

EXAMPLES

Example 1 (Inventive): Production of o-Aminobenzoic Acid with Yeast

Strains, Media and Growth Conditions.

The *Saccharomyces cerevisiae* TRP4 knock out strain was purchased from GE Healthcare Dharmacon Inc. If not denoted differently all chemicals were acquired from Sigma-Aldrich (Sternheim). *Saccharomyces cerevisiae* was grown under sterile conditions at 30° C. in YPD broth (bacteriological peptone, 20 g/L, yeast extract, 10 g/L, glucose, 20 g/L) supplemented with G418 (200 µg/mL) or defined Yeast Nitrogen Base (YNB) without Amino Acids Mineral Medium (ammonium sulfate, 5.0 g/L, biotin, 2.0 µg/L, calcium pantothenate, 400 µg/L, folic acid, 2.0 µg/L, inositol, 2.0 mg/L, nicotinic acid, 400 µg/L, p-aminobenzoic acid, 200 µg/L, pyridoxine HCl, 400 µg/L, riboflavin, 200 µg/L, thiamine HCL, 400 µg/L, citric acid, 0.1 g/L, boric acid, 500 µg/L, copper sulfate, 40 µg/L, potassium iodide, 100 µg/L, ferric chloride, 200 µg/L, magnesium sulfate, 400 µg/L, sodium molybdate, 200 µg/L, zinc sulfate, 400 µg/L, potassium phosphate monobasic, 1.0 g/L, magnesium sulfate, 0.5 g/L, sodium chloride, 0.1 g/L, calcium chloride, 0.1 g/L) supplemented with Yeast Synthetic Drop-out Medium Supplements without Tryptophan (adenine, 18 mg/L, myo-inositol, 76 mg/L, p-aminobenzoic acid, 8 mg/L, uracil, 76 mg/L, L-leucine, 380 mg/L, L-alanine, L-arginine, L-asparagine, L-cysteine, L-histidine, L-isoleucine, L-lysine, L-methionine, L-phenylalanine, L-proline, L-serine, L-threonine, L-tyrosine, Lvaline, 76 mg/L, each), G418 (200 µg/mL), α-D-glucose (20 g/L), and limiting amounts of L-tryptophan (5 mg/L for aerobic and 1.5 mg/L for anaerobic conditions, respectively). The strain was characterized in (fed)-batch fermenters (OmniFerm, HiTec Zang, Herzogenrath, Germany) with a cultivation volume of 1 L. Pre-cultures were inoculated from a glycerol stock [15% (v/v) glycerol] stored at −80° C. Seed train comprises a 3 ml YPD culture in a test tube at constant shaking at 200 rpm for 12 h (pre-culture I), a 50 ml YPD culture in a 1000 ml Erlenmeyer flask on a rotary shaker at constant shaking at 200 rpm for 8 h (pre-culture II) and a 50 ml YNB culture in a 1000 ml Erlenmeyer flasks on a rotary shaker at constant shaking at 200 rpm for 12 h (pre-culture III). Pre-culture II was inoculated by transferring 1 ml from pre-culture I into fresh sterile YPD medium of pre-culture II. Pre-culture III was inoculated to an optical density at 600 nm ($OD_{600}$) of 1 by transferring an appropriate amount of cells into a sterile conical centrifuge tube. After centrifugation (1,500×g, 5 min, RT) cells were suspended in sterile 1 ml saline (9 g/L sodium chloride) and transferred to the sterile YNB medium of pre-culture III. Procedure for inoculation of the fermenter to an $OD_{600}$ of 1 from pre-culture III was the same as described for inoculation of pre-culture III. For yeast cultivation under aerobic conditions initial stirring speed was set to 500 rpm and air was supplied at 0.2 L/min. For anaerobic conditions a constant stirring speed of 300 rpm was used and $N_2$ was supplied at 0.2 L/min. Oxygen and carbon dioxide levels in the exhaust gas of the fermenters were continuously monitored online using an off-gas analyzer (HiSense, HiTec Zang, Herzogenrath, Germany). For aerobic conditions dissolved oxygen was maintained at >30% air saturation by automatic adjustment of the stirring speed. For each condition pH was measured (Easyferm Plus VP 225, Hamilton Höchst, Germany) and maintained at 4.0 by automatic addition of 1.0 M $(NH_4)OH$ and 1 M HCl. For each condition the temperature was kept at 30° C. During the fermentation 1.5 ml samples were taken. An Eppendorf BioPhotometer (Eppendorf, Hamburg) was used for optical density measurements. An 1 mL aliquot of each sample was centrifuged for 5 min at 16,000×g (5415R; Eppendorf, Hamburg). Concentration of glucose, o-aminobenzoate and ethanol in the supernatant was determined with a CuBiAn XC (Optocell technology) biochemistry analyzer, HPLC-DAD (1100; Agilent Technologies, Santa Clara, USA), and GC-FID (7890A Agilent Technologies, Santa Clara, USA), respectively.

High Performance Liquid Chromatography

An Agilent 1100 series HPLC-DAD system [with diode array detector; Agilent Technologies, Santa Clara (USA)] was used to quantify the o-aminobenzoate concentration in culture supernatants. As stationary phase a C18 column Luna HPLC-column (4.6×250 mm; 3 pm; Phenomenex) was used at 20° C. with a binary solvent system consisting of methanol (solvent B) and water containing 0.1% (v/v) formic acid (solvent A). 10 µL of diluted culture supernatant was applied. Separation was achieved by the following gradient at a flow rate of 0.5 mL/min: 0-1 min, 2% B; 1-2 min, 2-10% B; 2-12 min, 10-70% B; 12-23 min, 70-90% B; 23-25 min, 90-98% B, 25-27 min, 98% B; 27-27.5 min, 98%-2% B; 27.5-30 min, 2% B. The o-aminobenzoate concentration was determined by peak integration at 254 nm (retention time: 18.9 min) and comparing to an external calibration curve.

Gas Chromatography

An Agilent 7890A GC-system [Agilent Technologies, Santa Clara (USA)] was used to quantify the ethanol concentration in culture supernatants. A Stabiwax-DB column (30 m×0.32 mm, ID 1 µm, Restek) was used. Separation was achieved by the following oven program: 0-3 min, 30° C.; 3-6 min, 40-150° C.; 6-8.4 min, 150-220° C. 1 µL of diluted culture supernatant was applied. Injector was set to 250° C. with a total flow of 787.43 mL/min and a split ratio of 100:1, resulting in a flow of 7.7666 ml/min. Signals were detected via FID set to 300° C.

Results and Discussion

Figure 1:
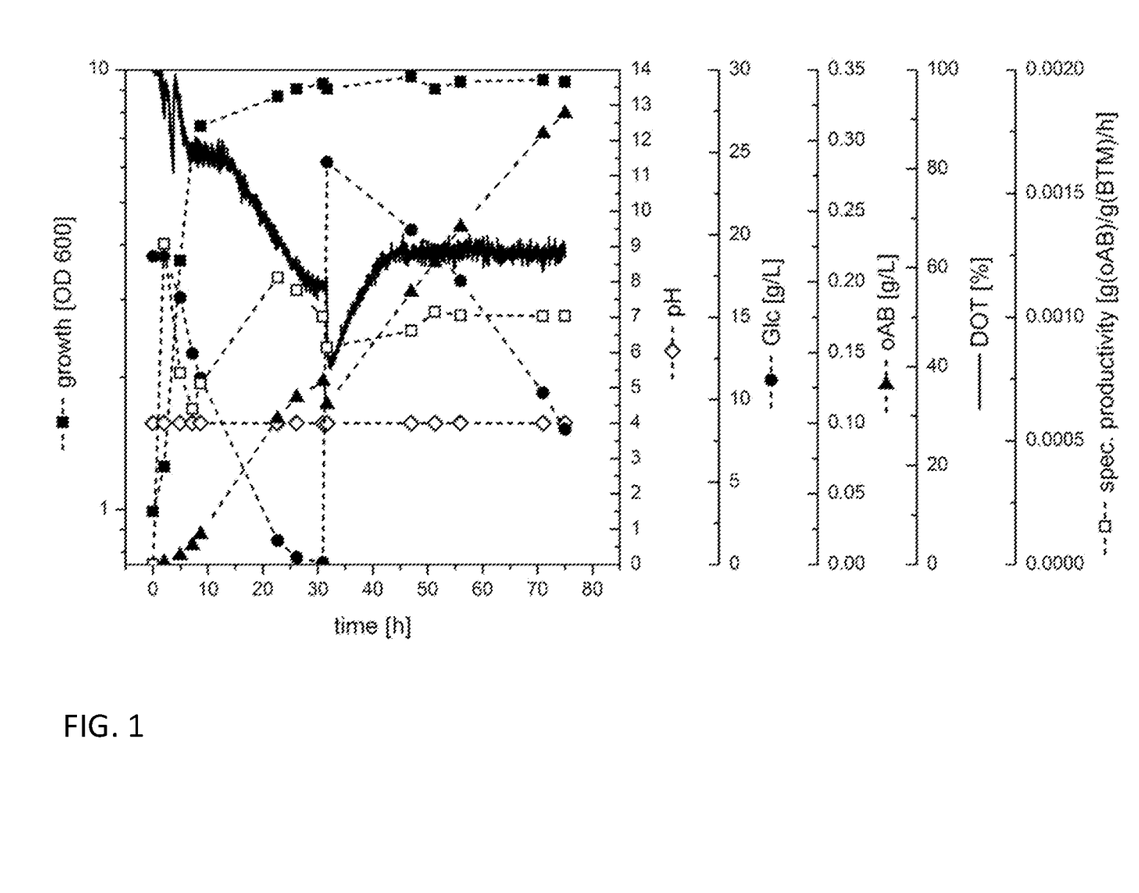
FIG. 1: Results of an aerobic fed batch fermentation with yeast as described in example 1.
Figure 2:
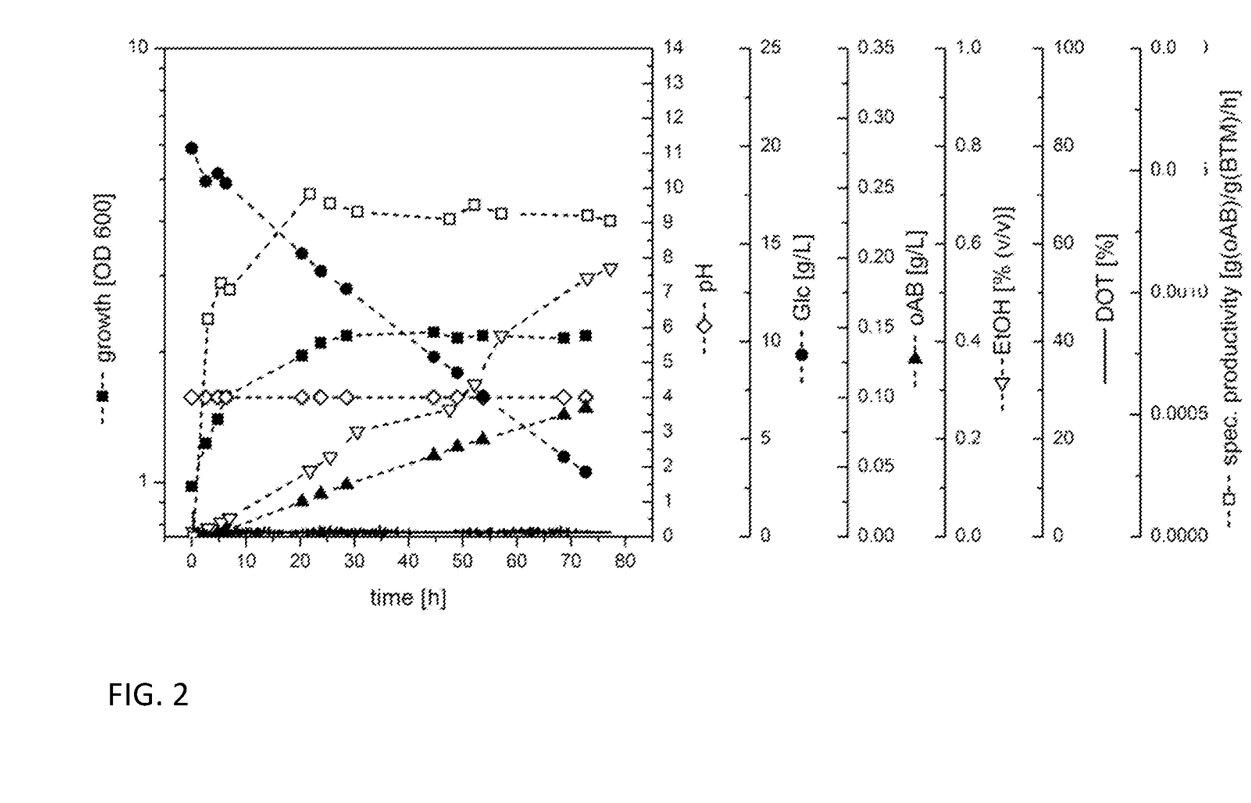
FIG. 2: Results of an anaerobic batch fermentation with yeast as described in example 1.

The yeast knock-out strain *Saccharomyces cerevisiae* TRP4 produced 320 mg/L o-aminobenzoic acid under aerobic conditions after 75 h of cultivation as determined by HPLC-DAD (254 nm). Under anaerobic conditions it produced 92 mg/L o-aminobenzoic acid after 73 h of cultivation. Production seems not to be coupled to growth since a constant accumulation of o-amonibenzoate during growth as well as in the stationary phase was observed. Assuming an $OD_{600}$ of 1 is correlated to a dry weight of 0.45 g/L, specific productivity of o-aminobenzoic acid in the stationary phase was about 1.0 and 1.3 mg $gDW^{-1}$ $h^{-1}$, under aerobic and anaerobic conditions, respectively. As expected, under anaerobic conditions a significant amount of ethanol was produced as determined by GC-FID.

The invention claimed is:

1. A method for producing o-aminobenzoic acid comprising the steps of
   a) fermenting at least one fermentable substrate in a fermentation vessel using a recombinant yeast cell comprising a knock out of the trp4 gene encoding anthranilate phosphoribosyltransferase and having no anthranilate phosphoribosyl transferase activity capable of converting the at least one fermentable substrate into o-aminobenzoic acid, wherein the fermentation in method step a) is performed at a pH between 2.0 and 5.0; and
      wherein said recombinant yeast cell produces more o-aminobenzoic acid than the wild type; and
   b) separating the produced o-aminobenzoic acid from the fermentation broth.

2. The method according to claim 1, wherein the separation of o-aminobenzoic acid in method step b) is performed after lowering the pH of the fermentation broth.

3. The method according to claim 1, wherein the fermentation vessel comprises a strirrer, and the separation of the produced solid o-aminobenzoic acid in method step b) is performed by adjusting the rotation speed of the stirrer in the fermentation vessel.

4. The method according to claim 1, wherein the separation of the produced solid o-aminobenzoic acid in method step b) is performed by filtration, settling, hydrocyclons and centrifugation.

5. The method according to claim 1, wherein the separation of the produced o-aminobenzoic acid in method step b) is performed by extraction with a suitable solvent.

6. The method of claim 5, wherein the o-aminobenzoic acid is extracted from fermentation broth which has been removed from the fermentation vessel.

7. The method of claim 5, wherein the solvent is added to the fermentation broth in the fermentation vessel.

8. The method according to claim 1, wherein the fermentation in method step a) is performed under anoxic conditions.

9. The method according to claim 1, wherein the fermentation in method step a) is performed at a pH of from 3.0 to 5.5.

10. The method according to claim 1, wherein a part of the o-aminobenzoic acid is produced during the stationary growth phase of the yeast cells.

* * * * *